United States Patent
Ahnblad et al.

(10) Patent No.: US 7,351,232 B2
(45) Date of Patent: Apr. 1, 2008

(54) NASAL RINSER AND OUTLET PORTION THEREFOR

(75) Inventors: Peter Ahnblad, Stockholm (SE); Susanne Lagerqvist, Bromma (SE)

(73) Assignee: ENTpro HB, Stockholm (SE)

( * ) Notice: Subject to any disclaimer, the term of this patent is extended or adjusted under 35 U.S.C. 154(b) by 223 days.

(21) Appl. No.: 10/069,595

(22) PCT Filed: May 14, 2001

(86) PCT No.: PCT/SE01/01055

§ 371 (c)(1),
(2), (4) Date: Jun. 4, 2002

(87) PCT Pub. No.: WO02/07665

PCT Pub. Date: Jan. 31, 2002

(65) Prior Publication Data

US 2002/0169422 A1    Nov. 14, 2002

(30) Foreign Application Priority Data

Jul. 25, 2000    (SE) .................................. 0002761

(51) Int. Cl.
*A61M 31/00* (2006.01)
*A61M 5/00* (2006.01)

(52) U.S. Cl. .................. 604/275; 604/514; 604/187
(58) Field of Classification Search ............... 604/217, 604/275, 239, 257, 514, 212, 93.01, 94.01, 604/181–183, 7, 523, 215, 264, 278, 294–295, 604/187, 279, 910; 606/199; 128/200.14
See application file for complete search history.

(56) References Cited

U.S. PATENT DOCUMENTS

| | | | | |
|---|---|---|---|---|
| 1,507,475 A | * | 9/1924 | Flagg .......................... | 604/212 |
| 2,485,184 A | * | 10/1949 | Blackman et al. ...... | 128/200.22 |
| 3,949,751 A | * | 4/1976 | Birch et al. ............ | 128/203.15 |
| 4,300,545 A | * | 11/1981 | Goodnow et al. ...... | 128/200.14 |
| 4,767,416 A | * | 8/1988 | Wolf et al. .................. | 604/239 |
| 4,815,666 A | * | 3/1989 | Gacka et al. ................ | 239/697 |
| 5,843,043 A | * | 12/1998 | Markus ....................... | 604/239 |
| 2002/0092521 A1 | * | 7/2002 | Sullivan et al. ......... | 128/200.24 |
| 2004/0116958 A1 | * | 6/2004 | Gopferich et al. .......... | 606/199 |

FOREIGN PATENT DOCUMENTS

JP    10043269 A    2/1998

* cited by examiner

Primary Examiner—Kevin C. Sirmons
Assistant Examiner—Elizabeth MacNeill
(74) Attorney, Agent, or Firm—Young & Thompson

(57) ABSTRACT

An outlet portion for nasal rinsers includes an outlet end, a connection end and a nozzle shaped channel, showing a restriction and an expanded outlet, in between.

11 Claims, 1 Drawing Sheet

U.S. Patent  Apr. 1, 2008  US 7,351,232 B2
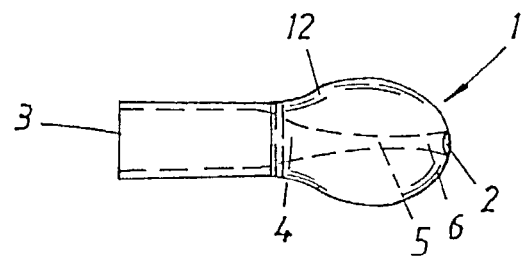
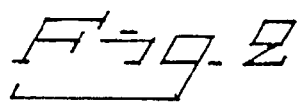
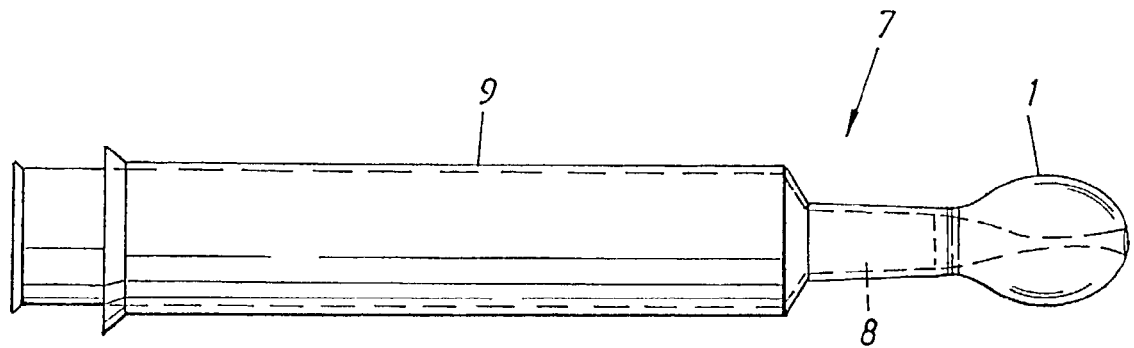
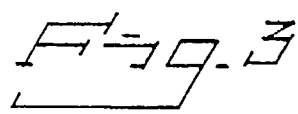
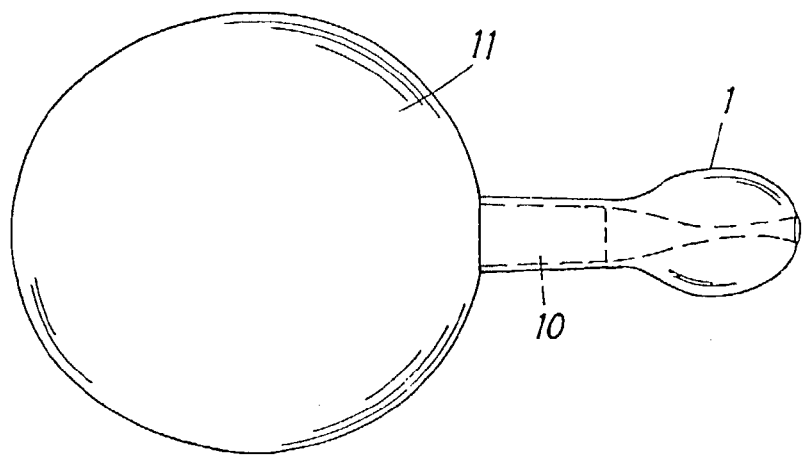

NASAL RINSER AND OUTLET PORTION THEREFOR

BACKGROUND OF THE INVENTION

The present invention relates to a nasal rinser and an outlet portion for a nasal rinser.

DESCRIPTION OF THE RELATED ART

Rinsing of the nose alleviate and reduce troubles with allergies, infections and troubles after nose surgery since the rinsing flushes away allergens (allergy-forming substance), microbes (virus, bacteria), bi-products of the body (pus, mucus) and dust and soot particles. The inflammatory swelling will be reduced and after nose surgery scabs will be loosened up, whereby the healing process will be accelerated. Rinsing of the nose with salt water is a well tried method and has been recommended by doctors for at least a hundred years.

The known nasal rinsers on the market are a potter container for multiple use, which is expensive, ungain and has a potter outlet, and two disposable variants which are prefilled with salt water and water from the Atlantic, respectively, which of course become very expensive to use on regular basis and whose outlet do not function satisfactory and therefore neither their ability to fill up the nose and the fact that they can only be used with the salt water that is prefilled in the nasal rinser.

SUMMARY OF THE INVENTION

A first object of the present invention is to provide an outlet portion for a nasal rinser that quickly, comfortably and in a well functioning way may fill the nasal cavity with liquid.

A second object of the present invention is to provide an inexpensive, simple and well functioning nasal rinser for multiple use.

The first object is met by means of an outlet portion for a nasal rinser, which is characterised in that it comprises an outlet end, a connection end and nozzle-shaped channel between these ends which shows a constriction and an expanded outlet. The outlet portion has the advantage that the liquid which is pressed in through the channel will leave the channel under turbulent flow, whereby the liquid quickly fills out the nasal cavity at the same time as a thin jet is avoided that sprays directly on the mucous membrane of the nasal cavity, which feels unpleasant.

The outlet portion preferably shows a circumference increased portion, for example a droplet or balloon shaped portion, at the outlet end so that the outlet portion seals against the edges of the nostril irrespective of the size of the nostril, which has the advantage that the liquid will not leak out the wrong way and that the shape of the outlet portion will help in opening up the nostril arch, which is the most narrow portion of the nostril.

Preferably, the outlet portion is made of a flexible material which is experienced as soft and comfortable against the nose, such as silicone rubber.

The shape of the channel at the connection end of the outlet portion is preferably adapted to the connection means of the nasal rinser, for example conical with the larges diameter at the end so that the outlet portion fits to a syringe having a conical tip.

The second object is met by means of a nasal rinser which is characterised in that it comprises an outlet portion of the present invention and a syringe or a compressible balloon for rinsing liquid, whereby the outlet portion is provided at the tip of the syringe or the outlet opening of the balloon, which is provided with connection means. A nasal rinser according to any one of the two variants is simple and inexpensive to manufacture and easy to use, especially the syringe variant where it is easy to suck in the rinsing liquid into the syringe before the nasal rinsing, and easy to keep clean, especially the syringe variant.

Of course, the outlet portion may be connected to any other type of nasal rinser means.

The rinsing liquid may for example be salt water, an oil emulsion or salt water provided with a medicine.

BRIEF DESCRIPTION OF THE INVENTION

The present invention will now be described by exemplifying embodiments of the present invention together with appended drawings, in which:

FIG. 1 illustrates an embodiment of an outlet portion according to the present invention of a nasal rinser.

FIG. 2 illustrates a first embodiment of a nasal rinser of syringe type according to the present invention.

FIG. 3 illustrates a second embodiment of a nasal rinser of balloon type according to the present invention.

DESCRIPTION OF THE PREFERRED EMBODIMENTS

In FIG. 1 a outlet portion 1 is shown, which comprises an outlet end 2 and a connection end 3. Between these ends 2, 3 a channel 4 is arranged. The channel 4 is nozzle shaped and shows a restriction 5 in the cross section and an expanded outlet 6. At the connection end 3 the channel 4 has a shape which is adapted to the type of connection of the nasal rinser at which the outlet portion shall be arranged. In the shown case the channel 4 is conically shaped with the largest diameter in the connection end to fot to a syringe with a conically tapering tip, for example a monoject syringe.

The outlet portion 1 has an outer shape that reminds of a lolly where the connection end 3 is the stick and the outlet end 2 is the lolly head. The outlet end 2 shows a circumference enlargement portion 12 which preferably is balloon or droplet shaped, whereby the outer diameter of the outlet portion increases from the outlet end 2 a distance inwards from this whereafter the outer diameter decreases. This results in the fact that the outlet portion 1 may be put into the nostril a short distance at the same time as the increasing diameter results in that the opening of the nostril fully is filled up by the outlet portion 1 so that it seals between the outlet portion 1 and the nostril. This design also results in that the outlet portion 1 suits all different sizes of nostrils.

Preferably the outlet portion 1 is made of a silicone rubber.

When rinsing liquid is pressed into the outlet portion 1 from for example a syringe into the channel 4 the pressure will increase when the liquid passs the restriction 5 and will thereafter increase in velocity when the liquid reaches in the expanded outlet, whereby the flow will become turbulent.

In FIG. 2 a nasal rinser 7 according to a first embodiment of the present invention is shown. It comprises an outlet portion 1 provided at the tip 8 of a syringe 9, in the shown case a monoject syringe with a conically shaped tip 8.

In FIG. 3 a nasal rinser according to a second embodiment of the present invention is shown. It comprises an outlet portion 1 provided at a hollow tip 10 at a balloon shaped body 11. The balloon shaped body 11, is compressible to be able to press out liquid comprised within the balloon shaped body 11 through the hollow tip 10 and out through the outlet portion.

At use lukewarm rinsing liquid is drawn into the syringe 9 or the balloon 11 through negative pressure, whereby it is pressed out through the outlet portion 1 and further into the nose.

The invention claimed is:

1. An outlet portion (1) for a nasal rinser, comprising:
   an outlet end (2), a connection end (3) and a nozzle shaped channel (4) between the outlet and connection ends configured for use as an outlet portion of a nasal rinser,
   the outlet end, the connection end, and the nozzle shaped channel being a unitary structure of one material,
   the nozzle shaped channel (4) having an internal hourglass shape comprising a channel restriction section (5) and an expanded channel outlet section (6), wherein,
   the outlet end terminates with a distal end of the expanded channel outlet section,
   the expanded channel outlet section expands toward the outlet end with a maximum interior diameter of the expanded channel outlet section being located at the distal end of the outlet end,
   in use, when a liquid entering the connection end is pressed through the restriction section, a pressure will increase when the liquid passes through the restriction section and a velocity increase when the liquid reaches the expanded channel outlet section so that the liquid leaves the outlet end under turbulent flow so that the liquid fills out a nasal cavity while avoiding a jet spraying directly on a mucous membrane of the nasal cavity,
   the nozzle shaped channel is housed in an enlarged circumferential portion (12) shaped to seal against edges of an interior of a user's nostril,
   an exterior of the enlarged circumference portion (12) is droplet or balloon shaped,
   an inner diameter of the expanded channel outlet section (6) is greater than an inner diameter of the channel restriction section (5),
   the connection end comprises an interior portion shaped to fit onto a conical tip,
   the connection end, the nozzle shaped channel, and the outlet end together define a straight passageway extending through a longitudinal axis from the outlet end to the connection end, and
   a largest cross-sectional exterior diameter of the connection end being less than a largest cross-sectional exterior diameter of the enlarged circumferential portion (12).

2. An outlet portion according to claim 1, wherein the channel (4) is conically shaped at the connection end (3) and has a largest diameter at the connection end (3).

3. An outlet portion according to claim 1, which is made of a flexible material.

4. A nasal rinser, characterised in that it comprises the outlet portion (1) according to claim 1 and a receptacle for rinsing liquid connected to the outlet portion (1), whereby the receptacle is maneuverable for emptying the rinsing liquid out through the outlet portion (1).

5. A nasal rinser according to claim 4, wherein the receptacle is provided with a piston for emptying of the rinsing liquid out through the outlet portion (1).

6. A nasal rinser according to claim 4, wherein the receptacle is a flexible, balloon shaped body, which is compressible for emptying of the rinsing liquid out through the outlet portion (1).

7. The outlet portion of claim 1, wherein the enlarged circumferential portion (12) is made of a silicone rubber.

8. An outlet portion (1) for a nasal rinser, comprising:
   a longitudinal axis and a channel extending throughout the longitudinal axis from a channel inlet (3) terminating a first distal end of the channel to a channel outlet (2) terminating a second, opposite distal end of the channel;
   the entirety of the outlet portion being a unitary structure of one material,
   an enlarged circumferential portion (12) housing an nozzle shaped channel portion (4) and including the channel outlet (2),
   the nozzle shaped channel portion (4) comprising a restriction section (5) connecting to an expanded channel outlet section (6) that expands towards and terminates at the distal end of the channel outlet (2) with the expanded channel outlet section increasing in interior diameter toward the second, distal end of the channel so that a maximum interior diameter of the expanded channel outlet section is located at the second, distalmost end of the channel,
   the nozzle shaped channel portion (4) being located in a part of the channel nearer the channel outlet than the channel inlet; and
   a connection end (3) connected to the enlarged circumferential portion (12) and including the channel inlet, the connection end comprising an interior portion shaped to fit onto a conical tip, wherein,
   a largest cross-sectional exterior diameter of the connection end is less than a largest cross-sectional exterior diameter of the enlarged circumferential portion (12),
   in use, when a liquid entering the connection end is pressed through the restriction section, a pressure will increase when the liquid passes through the restriction section and a velocity increase when the liquid reaches the expanded channel outlet section so that the liquid leaves the outlet end under turbulent flow so that the liquid fills out a nasal cavity while avoiding a jet spraying directly on a mucous membrane of the nasal cavity,
   the nozzle shaped channel portion is located within an end portion having a droplet or balloon exterior shape, and said outlet portion is configured for use as an outlet portion of a nasal rinser.

9. The outlet portion of claim 8, wherein the outlet portion is made of a silicone rubber.

10. An outlet portion (1) for a nasal rinser, comprising:
    a channel extending from a channel inlet (3) terminating a first distal end of the channel to a channel outlet (2) terminating a second, opposite distal end of the channel;
    an enlarged circumferential portion (12) housing a nozzle shaped channel portion (4) and including the channel outlet (2),
    the entirety of the outlet portion being a unitary structure of one material,
    the nozzle shaped channel portion (4) comprising a restriction section (5), the nozzle shaped channel portion (4) being located in apart of the channel nearer the channel outlet than the channel inlet,
    the restriction section (5) connecting to an expanded channel outlet section (6) that expands towards and terminates at the distalmost end of the channel outlet (2) with the expanded channel outlet section increasing in interior diameter toward the second, distal end of the channel so that a maximum interior diameter of the expanded channel outlet section is located at the second, distalmost end of the channel; and a connection end (3) connected to the enlarged circumferential portion (12) and including the channel inlet, the connection end comprising an interior portion shaped to fit onto a conical tip, wherein, a largest cross-sectional exterior diameter of the connection end is less than a largest cross-sectional exterior diameter of the enlarged circumferential portion (12), in use, when a liquid entering the connection end is pressed through the restriction section, a pressure will increase when the liquid passes through the restriction section and a velocity increase when the liquid reaches the expanded channel outlet section so that the liquid leaves the outlet end under turbulent flow so that the liquid fills out a nasal cavity while avoiding a jet spraying directly on a mucous membrane of the nasal cavity, the nozzle shaped channel portion is located within an end portion having a droplet or balloon exterior shape, and said outlet portion is configured for use as an outlet portion of a nasal rinser.

11. The outlet portion of claim 10, wherein the enlarged circumferential portion (12) is made of a silicone rubber.

* * * * *